(12) United States Patent
Robinson

(10) Patent No.: US 7,615,620 B2
(45) Date of Patent: Nov. 10, 2009

(54) DETECTION SYSTEM FOR PCR ASSAY

(75) Inventor: Philip S. Robinson, Aylesbury (GB)

(73) Assignee: KBiosciences Limited, Hoddesdon (GB)

( * ) Notice: Subject to any disclaimer, the term of this patent is extended or adjusted under 35 U.S.C. 154(b) by 0 days.

(21) Appl. No.: 11/443,547

(22) Filed: May 30, 2006

(65) Prior Publication Data

US 2007/0117108 A1 May 24, 2007

(30) Foreign Application Priority Data

May 28, 2005 (GB) ................................ 0510979.8

(51) Int. Cl.
*C07H 21/04* (2006.01)
*C12Q 1/68* (2006.01)
*C12P 19/34* (2006.01)

(52) U.S. Cl. .................... 536/23.1; 435/6; 435/91.2

(58) Field of Classification Search ............. 435/287.2, 435/91.2, 6; 536/24.31, 24.32, 24.33, 22.1
See application file for complete search history.

(56) References Cited

U.S. PATENT DOCUMENTS

| | | | | |
|---|---|---|---|---|
| 5,866,336 A | * | 2/1999 | Nazarenko et al. | 435/6 |
| 6,326,145 B1 | * | 12/2001 | Whitcombe et al. | 435/6 |
| 6,699,975 B2 | * | 3/2004 | Reed et al. | 534/558 |

FOREIGN PATENT DOCUMENTS

| | | | |
|---|---|---|---|
| DE | 199 34 084 A1 | | 1/2001 |
| DE | 102 50 948 A1 | | 5/2004 |
| EP | 0 909 823 A2 | | 4/1999 |
| EP | 1403382 A2 | * | 3/2004 |
| WO | 013399 A1 | | 5/1995 |
| WO | 049293 A3 | | 9/1999 |
| WO | 041549 A2 | | 7/2000 |
| WO | 030946 A1 | | 4/2002 |
| WO | 062422 A1 | | 7/2003 |
| WO | 003136 A2 | | 1/2004 |

OTHER PUBLICATIONS

Myakishev, MV et al. High-throughput SNP genotyping by allele-specific PCR with universal energy-transfer-labelled primers. Genome Research, vol. 11, pp. 163-169, 2001.*
Kong, D-M., et al., "Simulation of TaqMan by two single-labelled probes," Chem. Commun., 2584-2588, 2002.
Kong, D-M., et al., "Use of duplex probes simulating TaqMan to detect hepatitis B virus," New J. Chem., 2003, vol. 27, p. 721-726.
Koo, K., et al., "Detection of Listeria monocytogenes from a Model Food by Fluorescence Resonance Energy Transfer-Based PCR with an Asymmetric Fluorogeic Probe Set," Appl. Env. Micriobio., 2003, p. 1082-1088.
Koo, K., and Jaykus, L.-A., "Detection of single nucleotide polymorphisms within the Listeria genus using an asymmetric fluorogenic probe set and fluorescence resonance energy transfer based-PCR," Lett. Appl. Micriobiol., 2002, vol. 35, 513-517.
Solinas, A., et al., "Duplex Scorpior primers ins SNP anaysis and FRET applications," Nucleic Acid Rsch., 2001, vol. 29, No. 20 e96 (9 pages).
Purcell, P., Search Report in respect of GB0510979.8, searched Mar. 31, 2006, The Patent Office (UK).
Purcell, P., Search Report in respect of GB0610653.8, searched Sep. 1, 2006, The Patent Office (UK).
Santagati, F., Search Report in respect of EP 06252796, searched Jul. 19, 2006, European Patent Office.
F. Santagati, European Patent Office, Communication pursuant to Article 94(3) EPC, in respect of Application No. 06 252 796. 5—1222, mailed Apr. 17, 2008.

* cited by examiner

*Primary Examiner*—Suryaprabha Chunduru
(74) *Attorney, Agent, or Firm*—Bradley N. Ruben

(57) ABSTRACT

The present invention provides a detection system for a PCR process using FRET which comprises at least two single-labelled Oligonucleotide sequences of differing Tm that hybridize to one another in free solution to form a fluorescent quenched pair, that upon introduction of a complementary sequence to one or both sequences generates a measurable signal, one of the sequences being of a Tm that is below the Ta of the PCR process, the other not being below the Ta of the PCR process.

19 Claims, 14 Drawing Sheets

Fig. 1A  Indirect detection of DNA sequence

1   -Reaction components  - Taq DNA polymerase
                          - deoxy nucleotides triphosphates dNTP's
                          - Reaction Buffer
                                                                    Genomic DNA Tailed non labelled                 Quencher 3' labelled
   Oligo                               Oligo antisense to fluorophore labelled oligo Reverse unmodified                  Fluorophore 5' labelled
   Oligo                               Oligo identical sequence to tailed
                                       non labelled oligo 2   1st round of thermal cycling – forward tailed primer hybridises to genomic DNA and quencher oligo
    is hybridised to fluorophore labelled oligo. Reverse primer hybridises to genomic DNA (not shown)

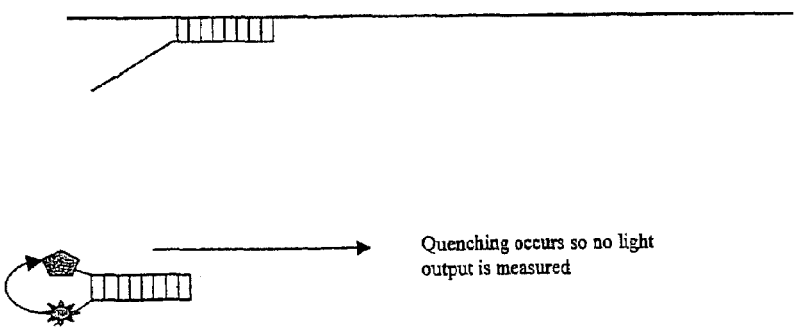

Quenching occurs so no light
output is measured

3   DNA synthesis occurs copying genomic DNA incorporating the tail sequence into the synthesised strand + DNA strand

- DNA strand

Quenching occurs so no light output is measured

4   Synthesised strand DNA is copied inclusive of primer tail. Reverse strand copied from more tailed pr

REPLACEMENT SHEET

Quenching occurs so no light output is measured

5  DNA synthesis is initiated from fluorescent labelled primer

Fluorescent oligo no longer quenched gives light output

Quencher oligo no longer able to hybridise to fluorescent labelled oligo

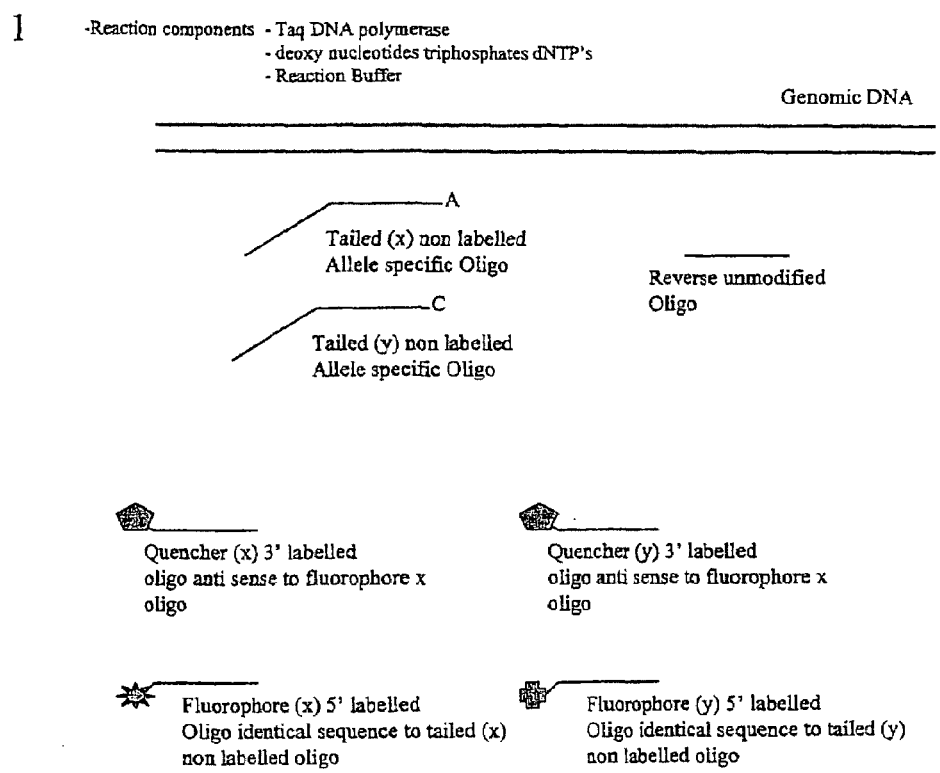
Fig. 2A Indirect detection of DNA sequence SNP Genotyping 2   1st round of thermal cycling – Depending on genotype of DNA under test either or both forward tailed primer hybridise to genomic DNA and quencher oligos are hybridised to their complementary fluorophore labelled oligo. Reverse primer hybridises to genomic DNA (not shown). Example shows heterozygous individual Quenching occurs so no light output is measured 3  DNA synthesis occurs from both allele specific oligos copying genomic DNA incorporating the x and y tail sequences into the synthesised strands. The reverse strand is not shown.

4    Synthesised strand DNA is copied inclusive of primer tails. Reverse strand is also primed and copied from more tailed allele specific primer (not shown)

X tail incorporated DNA strand

Y tail incorporated DNA strand

Quenching occurs so no light output is measured

Fig. 2E

5   DNA synthesis is initiated from both x and y
    fluorescent labelled primers

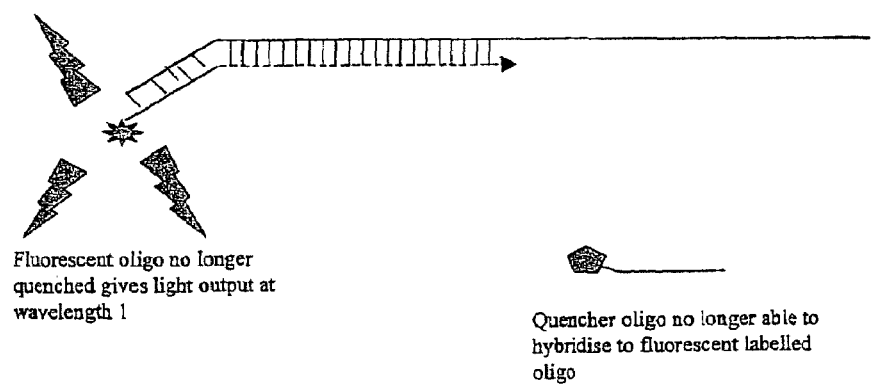

Fluorescent oligo no longer
quenched gives light output at
wavelength 1

Quencher oligo no longer able to
hybridise to fluorescent labelled
oligo

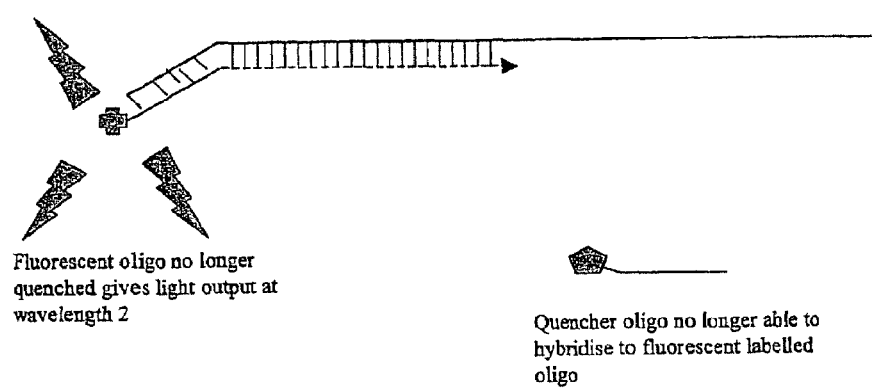

Fluorescent oligo no longer
quenched gives light output at
wavelength 2

Quencher oligo no longer able to
hybridise to fluorescent labelled
oligo

Fig. 3A -- Direction detection of DNA sequence using 5' nuclease assay

1     -Reaction components - Taq DNA polymerase
- deoxy nucleotides triphosphates dNTP's
- Reaction Buffer Genomic DNA Non labelled forward
Oligo Quencher 3' labelled
Oligo anti sense to reporter probe Non labelled reverse
Oligo Fluorophore 3' labelled
Oligo reporter probe 2     1st round of thermal cycling – forward and reverse primers initiate synthesis of region of interest creating double stranded DNA. Reporter probe and quencher oligos are hybridised together.

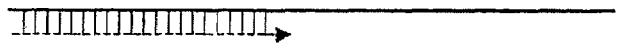

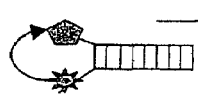     Quenching occurs so no light output is measured

3    The reporter probe hybridises to the amplified region. It is unable to be extended by the Taq polymerase and is therefore degraded by the 5' nuclease, thus producing light from the now unquenched fluorophore.

Fig 4A -- Semi direct detection of DNA sequence

1 -Reaction components - Taq DNA polymerase
 - deoxy nucleotides triphosphates dNTP's
 - Reaction Buffer Genomic DNA

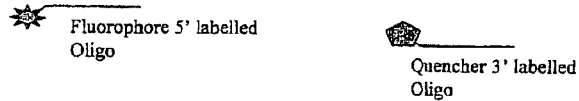
Fluorophore 5' labelled
Oligo

Quencher 3' labelled
Oligo

Reverse unmodified
Oligo

2 Pre-thermal cycling --quencher oligo is hybridised to fluorophore labelled oligo.

Quenching occurs so no light
output is measured

3     DNA synthesis is initiated from fluorescent labelled primer

Fluorescent oligo no longer quenched gives light output

Quencher oligo no longer able to hybridise to fluorescent labelled oligo

SEQUENCE LISTING

<160> NUMBER OF SEQ ID NOS: 9

<210> SEQ ID NO 1
<211> LENGTH: 36
<212> TYPE: DNA
<213> ORGANISM: Artificial
<220> FEATURE:
<223> OTHER INFORMATION: 5' (6-Carboxy Fluorescein)-labelled primer

<400> SEQUENCE: 1
gtgtgctagc gtcctgaagg tgaccaagtt catgct           36

<210> SEQ ID NO 2
<211> LENGTH: 36
<212> TYPE: DNA
<213> ORGANISM: Artificial
<220> FEATURE:
<223> OTHER INFORMATION: 5' (6-carboxy-4',5'-dichloro-2',7'-
      dimethoxyfluorescein)-labelled primer

<400> SEQUENCE: 2
atcggtagca tcgctgaagg tcggagtcaa cggatt           36

<210> SEQ ID NO 3
<211> LENGTH: 41
<212> TYPE: DNA

```
<213> ORGANISM: Artificial
<220> FEATURE:
<223> OTHER INFORMATION: allele-specific PCR primer 1 for example

<400> SEQUENCE: 3
gaaggtgacc aagttcatgc tgcaggaggc cgcactctct a                           41

<210> SEQ ID NO 4
<211> LENGTH: 40
<212> TYPE: DNA
<213> ORGANISM: Artificial
<220> FEATURE:
<223> OTHER INFORMATION: Allele-specific PCR primer 2 for example

<400> SEQUENCE: 4
gaaggtcgga gtcaacggat tcaggaggcc gcactctctg                             40

<210> SEQ ID NO 5
<211> LENGTH: 28
<212> TYPE: DNA
<213> ORGANISM: Artificial
<220> FEATURE:
<223> OTHER INFORMATION: PCR reverse primer

<400> SEQUENCE: 5
atagcactaa cagaagacag atcgctaa                                          28

<210> SEQ ID NO 6
<211> LENGTH: 15
<212> TYPE: DNA
<213> ORGANISM: Artificial
<220> FEATURE:
<223> OTHER INFORMATION: Black Hole Quencher 1a (non-fluorescent
      quenching moiety) primer complementary to 5Fam labelled prim

<400> SEQUENCE: 6
aggacgctag cacac                                                        15

<210> SEQ ID NO 7
<211> LENGTH: 15
<212> TYPE: DNA
<213> ORGANISM: Artificial
<220> FEATURE:
<223> OTHER INFORMATION: Black Hole Quencher 1a (non-fluorescent
      quenching moiety) labelled Joe quenching primer

<400> SEQUENCE: 7
agcgatgcta ccgat                                                        15

<210> SEQ ID NO 8
<211> LENGTH: 18
<212> TYPE: DNA
<213> ORGANISM: Artificial
<220> FEATURE:
<223> OTHER INFORMATION: 18mer artificial BHQ1a labelled Fam
      quenching primer

<400> SEQUENCE: 8
ttcaggacgc tagcacac                                                     18

<210> SEQ ID NO 9
<211> LENGTH: 18
<212> TYPE: DNA
<213> ORGANISM: Artificial
<220> FEATURE:
<223> OTHER INFORMATION: 18mer BHQ1a labelled Joe quenching primer
```

-continued

```
<400> SEQUENCE: 9
ttcagcgatg ctaccgat                                                        18
```

DETECTION SYSTEM FOR PCR ASSAY

FIELD OF THE INVENTION

This invention relates to a new Fluorescence Resonance Energy Transfer (FRET)-based detection system suitable for use in polymerase chain reaction assays.

BACKGROUND TO THE INVENTION

The discovery of the polymerase chain reaction (PCR) has revolutionised the field of molecular biology allowing for the amplification of any desired stretch of DNA from any organism.

More specialised use of PCR is seen in the areas of real-time quantitation and in end point determination of Genotypes where the use of homogeneous assay systems is employed. A homogeneous assay system is one where to derive the result of the reaction does not require the physical separation of the reaction components away from each other. In other words the reaction is conducted and the results derived with no further physical intervention into the reaction.

When monitored in real-time (in other words, monitoring the production of product at every cycle during the PCR process) PCR can be used in a quantitative manner. This has wide application in many fields from diagnosis of viral infections to determination of the abundance of a messenger RNA species within human RNA. The physical process of monitoring real time PCR is complex, requiring sophisticated instrumentation specifically designed for the process. This instrumentation requires the PCR process to produce a measurable amount of light increasing with every cycle until the reaction components are exhausted. To serve this need a number of elegant approaches have been demonstrated and commercially exploited. Two such examples of these are the Taqman 5' nuclease assay marketed by Applied Biosystems (USA) and the SybRGreen detection chemistry marketed by Molecular Probes (Netherlands). Both Quantitative PCR systems work well, but both have drawbacks that would benefit from being overcome.

Genotyping (in particular Single Nucleotide Polymorphism (SNP) Genotyping) on the other hand is a process that is less demanding on the instrumentation. The process is essentially the same employing the use of a homogeneous assay system, but the requirement for monitoring the reaction products at each cycle of the PCR is less critical. Indeed, the majority of scientists conducting SNP Genotyping using fluorescence based systems conduct the PCR and only at the end of the reaction do they determine the levels of product made. This is generally termed end-point analysis. SNP Genotyping has a further level of complexity, in that the purpose of the reaction is to determine the individual DNA genotype at a single locus within their genome. SNP's are biallelic markers that are ideally suited to being determined by fluorescent homogeneous assays in large numbers at low cost. The various reaction systems that are currently in use are again the Taqman reaction (Applied Biosystems), the Amplifluor system (Serologicals, USA) and the Scorpions system (DxS, UK). All are elegant reaction systems producing good quality data, but each has its own drawback.

The principle of all the homogeneous assay systems is to use the physical process of Fluorescence Resonance Energy Transfer (FRET) to detect the production of product in the PCR process. FRET is the process whereby when two fluorophores are in close enough proximity to each other that they will undergo an energy transfer exchange when excited by light at wavelengths matched to their particular excitation wavelength. FRET is ideally suited to the quantitation of PCR as it allows for the reaction to be monitored without being separated, a process that would be impossible bearing in mind that in general 40 cycles of PCR are carried out and the amount of product needs to be determined after each cycle.

The main techniques currently in use work well but suffer a number of drawbacks that hamper their use in the scientific world.

The Applied Biosystems Taqman assay as discussed in, for example, U.S. Pat. No. 5,538,848 (or, more generally, a FRET based 5' nuclease assay), requires the production of a dual labelled Oligonucleotide probe for each DNA sequence to be measured. This probe in its pre-reaction state is termed 'quenched'. In other words two fluorophores (or one non-fluorescent quencher and a fluorophore) are attached to a short Oligonucleotide within approx 30 nucleotides of each other. This distance is small enough that when one of the fluorophores is excited at its optimal wavelength the other fluorophore absorbs the energy absorbed and emits light at a different wavelength, or in the case of a non-fluorescent quencher the absorbed energy is passed by FRET to the non-fluorescent quencher and no light is emitted. When this molecule is included in the reaction the PCR process creates DNA complementary to it. This allows the probe to bind to the DNA whereby it is subsequently destroyed by the 5' nuclease activity of the Taq polymerase used in the PCR process. Now the probe is degraded the two fluorophore pairs are no longer in close enough proximity to undergo FRET and a measurable light difference is created.

The main drawback with the Taqman assay is the requirement for the production of the dual labelled Oligonucleotide probes. A single probe is required for quantitative measurements of DNA mass, whereas two are required for SNP genotyping (one for each allele). The production of the probe itself is a costly and timely process. At time of writing each probe can cost as much as £250, yielding enough reagent for only a few thousand reactions. If one is to consider that in a SNP Genotyping project anywhere upwards of 200 SNP's can be studied, then this would require an initial investment of £10,000 in probe production. This is a prohibitively large sum for many science organisations, and thus a major drawback of the system.

In the area of quantitative gene expression the use of SYBR Green is often employed as a low cost alternative to the use of Taqman. SYBR Green is an interchelating dye that only binds double stranded DNA. As such it can be employed in quantitative homogeneous PCR assays. The PCR product is generated as the cycle number in the reaction increases, and as the product builds up the SYBR Green binds to the product. Once bound the SYBR Green undergoes a conformational change and exhibits fluorescence which is directly measured. The main two drawbacks to the use of this technique are the non-specific nature of the reaction, in that any product whether it is the correct product or not will produce a signal. It is therefore imperative to confirm that the PCR produces the amplicon that is required to be measured. Taqman does not suffer from this drawback as the probe interacts with the sequence of the correctly generated amplicon only. Secondly, the use of SYBRgreen is known to be difficult to optimise as the SYBR green itself can interact with the PCR process making the reaction difficult to optimise.

The Amplifluor and Scorpion homogeneous PCR assay systems also suffer from similar drawbacks. Both systems utilise a tailed PCR primer to interact with a hairpin quenched fluorescent primer. In other words the PCR reaction is initiated with conventional oligonucleotide primers of which one (or two in the case of allele specific PCR based SNP genotyping) contains a sequence that is identical to the 3' end of the Amplifluor or Scorpion fluorescent primers. The reverse complement to this sequence is then made during the first few cycles of the PCR reaction. This allows the fluorescent primers to then initiate the PCR reaction. Upon doing this the hairpin structure of the Amplifluor or Scorpion primers is copied and 'unravelled'. These hairpin structures contain fluorescent quencher pairs, that are fully quenched when the hairpin structure can form, however when this is copied the structure can no longer form, and hence the fluorophore quencher pair is separated and fluorescent signal is generated. A number of modes of operation exist for both Amplifluor and Scorpion technology, however they suffer from at least one or more of the following drawbacks. Each hairpin-based primer is again difficult and costly to synthesise, due to the complex nature of the hairpin and dual labelled fluorophore quencher pairs. This cost and technically demanding nature of the synthesis is a major drawback. Further to this the reaction is also susceptible to the generation of signal from non-specific PCR artefacts such as primer dimer, and incorrect amplicon generation.

Further alternative assays are disclosed in the following patent applications: PCT WO00/41549; EP 0,909,823; PCT WO02/30946; PCT WO99/49293; and DE 10230948.

The need for an easy to synthesise, low cost and relatively reliable specific detection system for homogeneous PCR assays is apparent. It is a general objective of the present invention to address one or more of these aforementioned shortcomings of the existing FRET-based detection systems for PCR. The following invention addresses these in a number of different formats, providing a detection system suitable for the detection of PCR products directly or indirectly and which may be used in a quantitative, real-time and/or end point manner.

SUMMARY OF THE INVENTION

According to a first aspect of the present invention there is provided a detection system using FRET which comprises at least two single-labelled oligonucleotide sequences of differing Tm that hybridise to one another in free solution to form a fluorescent quenched pair, that upon introduction of a complementary sequence to one or both sequences generates a measurable signal, one of the sequences being of a Tm that is below the Ta of the PCR process. The other has a Tm that is suitably not below the Ta but preferably is substantially above it.

A primary problem with the above-discussed prior art techniques is linked to the synthesis of dual labelled fluorescent oligos. The current invention takes advantage of the low cost high throughput and ease of synthesis of single fluorescent-labelled oligos. These oligos are very significantly easier to synthesise on automated synthesisers. The associated cost is typically an order of magnitude cheaper than a dual fluorescent-labelled probe. Furthermore, by use of oligo sequence pairs of which one sequence, suitably the quencher sequence, has a Tm (melting temperature) below the Ta (annealing temperature) of the PCR process, the effectiveness of the technique is dramatically improved.

A commonly used formula for determining the Tm of a sequence is Tm=4(G+C)+2(A+T), and thus the low Tm of one sequence may, in principle, be attained by a shorter length and/or a reduced (G+C)/(A+T) ratio relative to the other sequence of the reporter pair. It is preferred that one of the sequences be more than 10 bases longer than the other and preferably at least 15 bases longer.

The invention is applicable in a number of formats, which will be addressed separately below. The invention embraces a method of performing a FRET assay as well as a kit for the purpose.

BRIEF DESCRIPTION OF THE DRAWINGS

Preferred embodiments of the present invention will now be more particularly described by way of example with reference to the accompanying drawings wherein.

DESCRIPTION OF THE PREFERRED EMBODIMENTS

Embodiment 1

Figure 1B:
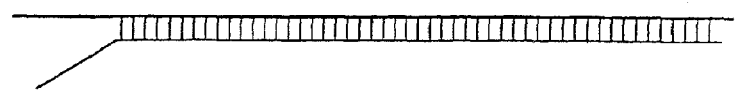
FIG. 1 is a simple reaction schema for indirect detection of a DNA sequence embodying the method of the present invention.
Figure 1B:
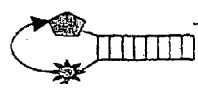
Figure 1B:
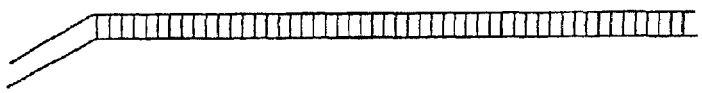
Figure 1B:
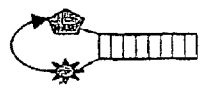
Figure 1C:
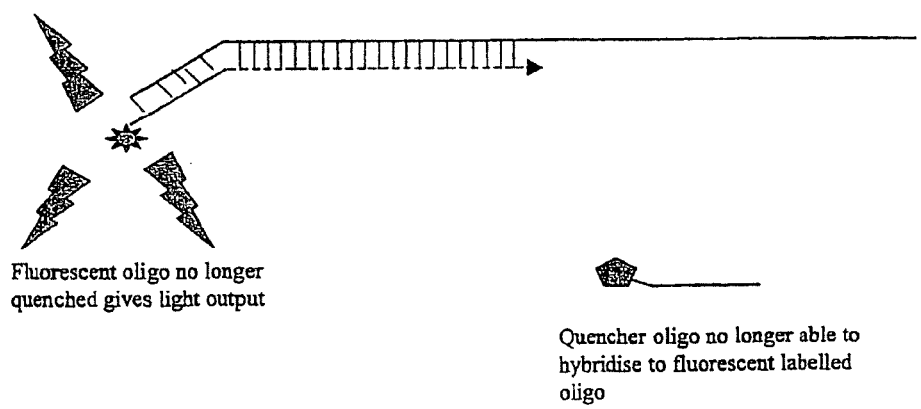
Figure 2B:
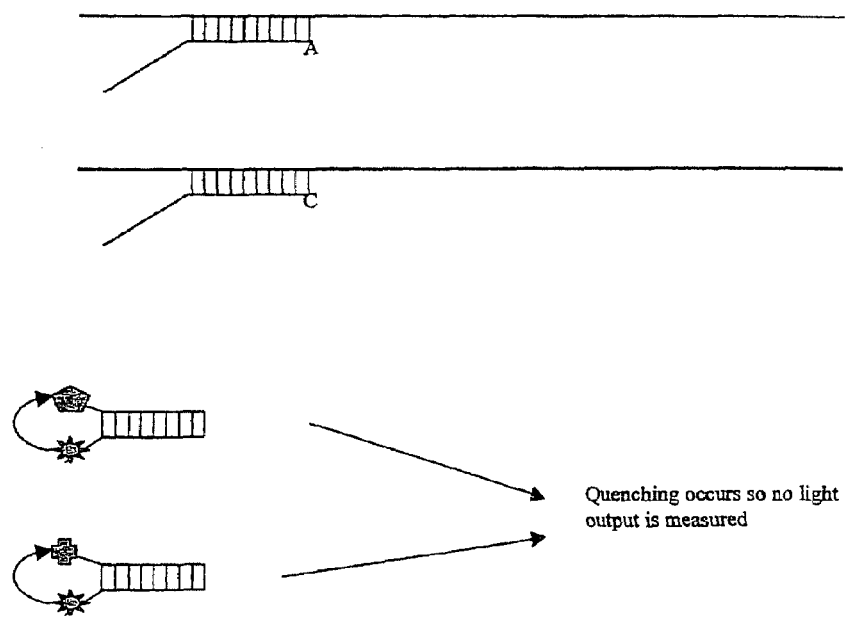
FIG. 2 is a simple reaction schema for indirect detection of a DNA sequence embodying the method of the present invention.
Figure 2C:
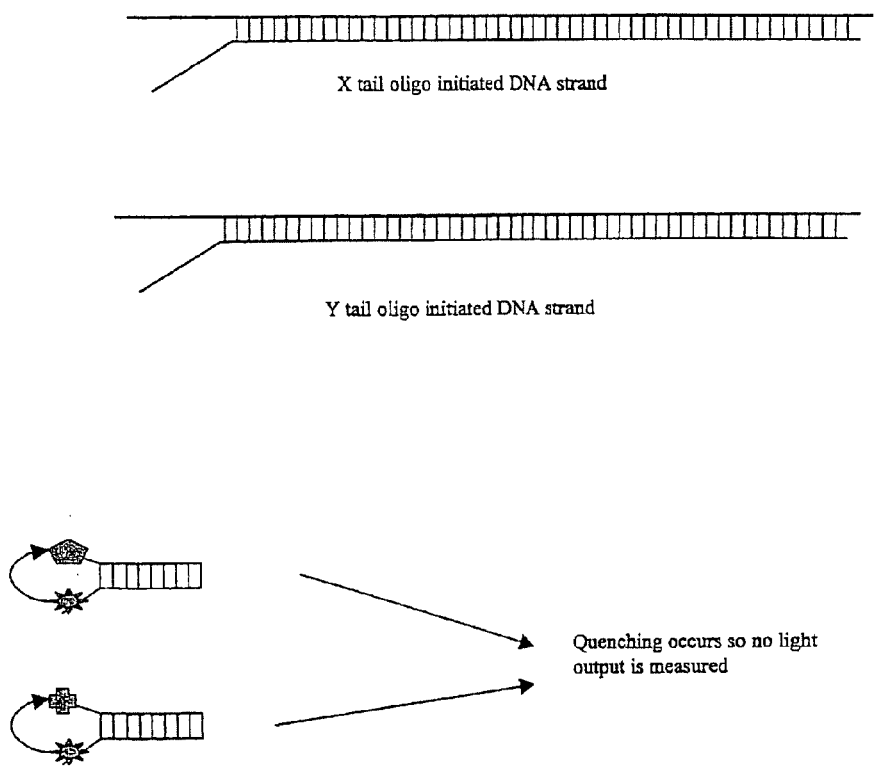
Figure 2D:
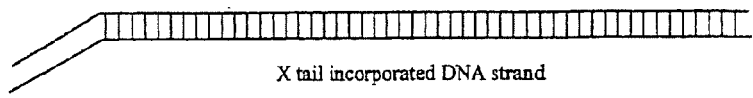
Figure 2D:
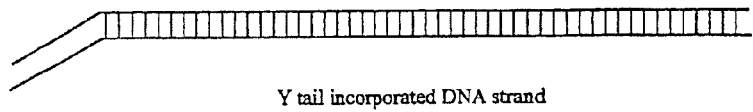
Figure 2D:
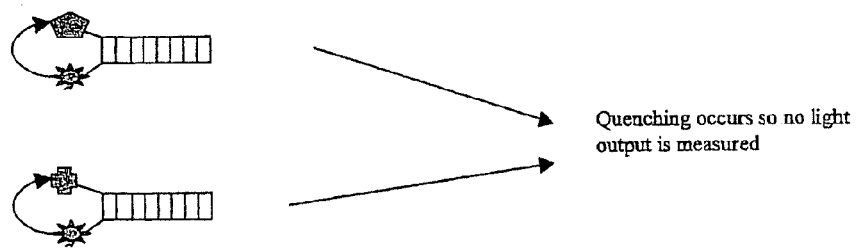

Use in Indirect Detection of PCR Products

This embodiment, illustrated in FIG. 1 hereinafter, utilises a conventional oligo (primer) to initiate the PCR process. This conventional primer is tailed with a DNA sequence that is not directed to the amplicon region of interest, whereby this tail is essentially inert. This tail sequence is positioned at the 5' portion of the primer. The 3' portion of the primer is directed to the amplicon region of interest and therefore drives the specificity of the reaction. Also included in the reaction is a single fluorescent-labelled Oligo that is identical in sequence to the tail region of the conventional primer. A number of suitable fluorophores exist, with a popular choice being Fam (a derivative of fluorescein). Finally, included in the reaction is a 3' quencher labelled Oligo antisense to the Fam labelled Oligo. A number of suitable labels exist of which the Black Hole quencher series of labels are a popular choice.

Due to the complementarity of the two-labelled Oligos they hybridise to each other. This hybridisation brings the quencher label in very close proximity to the fluorophore, thereby rendering all fluorescent signal from the Fam molecule quenched when excited at 488 nm (the optimal excitation wavelength of Fam). The PCR process is then initiated and PCR product begins to be generated. After the first few cycles of PCR the antisense sequence to the fluorescent primer is generated. The fluorescent PCR primer is then able to initiate synthesis during the PCR, and does so. This produces amplicon with a 5'Fam molecule. Once this occurs the quenching oligo is no longer able to hybridise to the Fam labelled oligo as the PCR process produces double stranded amplicon DNA. As the quenching oligo can no longer hybridise to the Fam oligo, signal is then generated which is directly proportional to the amount of PCR product generated. As noted above, the five stages of this reaction schema are illustrated in FIG. 1.

Embodiment 2

End Point Analysis of Allele Specific SNP Genotyping

This embodiment, illustrated in FIG. 2, utilises the same fluorophore/quencher Oligo pair as in the first embodiment. The reaction schema is identical but for a few modifications.

To achieve SNP Genotyping requires the use of two fluorescent-labelled primers and corresponding quencher Oligos. Each primer is again tailed with a unique sequence, to which in the reaction is included a 5' fluorescent labelled primer. Two suitable dyes are Fam and Joe, both derivatives of Fluorescein but spectrally resolvable from each other. The two primers (non tailed portion) are (generally termed forward) directed to the DNA of interest. In this portion of the primer they typically differ only by a single nucleotide at their 3' terminal base. Each primer is directed to the polymorphic base in the DNA of interest. PCR is conducted and the two primers only initiate synthesis when the 3' base is perfectly matched. When a mismatch occurs synthesis does not proceed.

During the reaction the specific tail depending on the genotype is able to initiate synthesis (or both are, in the case of a heterozygote). This again incorporates the fluorescent tail portion of the primer in to the PCR product thereby hindering the hybridisation of the quencher Oligo. Signal is therefore generated according to which of the Oligos has initiated the synthesis. The reaction is then read on a fluorescent plate reader for both fluorophores. Their resulting data is then plotted and a cluster plot of one fluorophore over the other is generated. The resulting genotypes are then able to be determined based on the cluster plots.

Embodiment 3

Direct Detection of PCR Products

Specific Detection of PCR products is the most robust method for ensuring the accurate monitoring of a presence of DNA region of interest. The Taqman assay is one of the most widely used methods however it is expensive to perform, due to the requirement for double labelled probes.

Figure 3B:
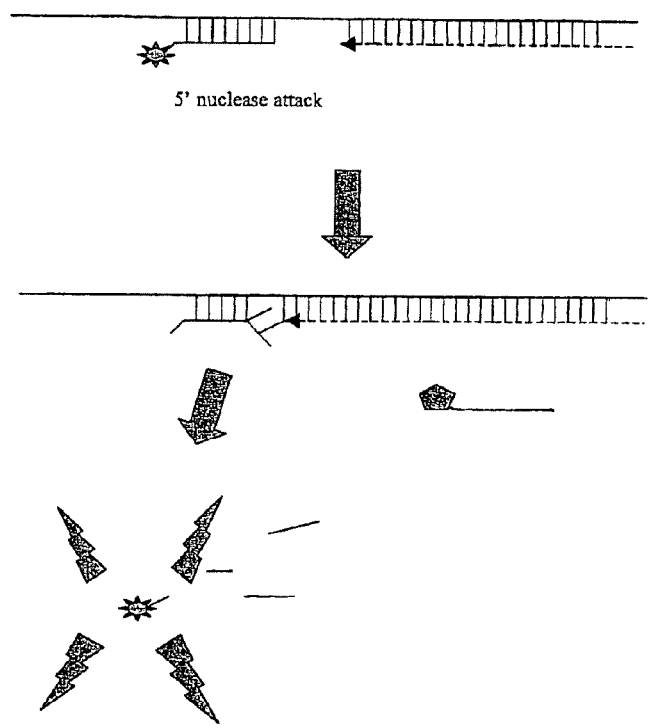
FIG. 3 is a simple reaction schema for indirect detection of a DNA sequence in SNP Genotyping embodying the method of the present invention.
Figure 4B:
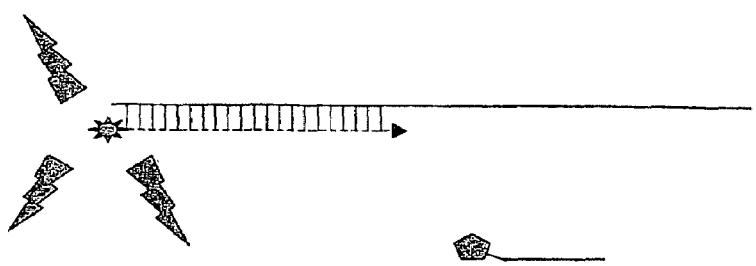
FIG. 4 is a graph of Fam signal divided by Rox on the X axis, and Joe signal divided by Rox on the Y axis for Experimental Example 1 that embodies the use of a low Tm primer in the probe pair.

It is possible using the current invention of separating the probe into two single labelled Oligos to perform Taqman assays thereby overcoming this cost limitation. The Taqman assay is a trademark name for the 5' nuclease assay. The 5'nuclease assay utilises the 5'-3' exonuclease activity of DNA polymerases and more specifically Taq polymerase. During the PCR if the enzyme encounters a probe sequenced annealed to the amplicon to be copied it displaces the probe and degrades it. This degradation is monitored by the use of FRET as previously described. A simple schema for this embodiment is illustrated in FIG. 3.

To perform a 5' nuclease assay with this invention is straightforward. A single fluorophore labelled fluorescent probe is created and the antisense quencher labelled pair to that probe is also created using traditional DNA synthesis techniques. The probes are respectively modified at their 3' end with the fluorophore or quencher group. Other than this the quencher labelled sequence differs from the fluorophore labelled fluorescent probe sequence substantially only in that it is shorter by at least ten nucleotides and preferably 15 or more nucleotides whereby compared to the fluorophore labelled fluorescent probe sequence it has a relatively low Tm and which is below the annealing temperature for the PCR.

In the pre thermal cycling reaction mix the two probes are hybridised to each other, thus being a fully quenched probe. During the PCR the longer probe will be subjected to the 5' nuclease activity of the DNA polymerase. This results in degradation of the longer probe, thus removing the quenching of the fluorophore signal, leading to a measurable and quantitative increase in fluorescence when the Tm is lowered to a point where the shorter sequence is able to hybridise.

A further use of the fluorophore quencher pair Oligo system described is in the homogeneous detection of PCR products without the use of 5' nuclease activity. The same reaction is developed with the exception that either or both the fluorophore and quencher Oligos are modified with a chemical group (such as a phosphate group) that inhibits the degradation by the 5' nuclease activity of Taq. In this case the fluorescent signal is generated by the fact that as the PCR product builds up either or both of the probes are able to hybridise with themselves or the PCR product generated when the reaction temperature is dropped below the Tm of the shorter labelled sequence. When either or both bind to the PCR product generated. the fluorophore labelled Oligo is no longer quenched thus producing a measurable signal.

An example of reduction to practice of allele specific PCR based genotyping utilising the invention is presented below.

EXAMPLE 1

Notation—_Fam=6-Carboxy Fluorescein; Joe=6-carboxy-4',5'-dichloro-2',7'-dimethoxyfluorescein;
BHQ1a=Black Hole Quencher 1a (non fluorescent quenching moiety)

Seven oligo nucleotide primers were designed and their sequences can be found below.
1. Fam labelled primer—SEQ ID NO: 1 5' Fam—gtgtgctagcgtcctgaaggtgaccaagttcatgct
2. Joe labelled primer—SEQ ID NO: 2 5' Joe—atcggtagcatcgctgaaggtcggagtcaacggatt
3. Allele specific Primer 1—SEQ ID NO: 3 5' gaaggtgaccaagttcatgctgcaggaggccgcactctcta
4. Allele specific Primer 2—SEQ ID NO: 4 5' gaaggtcggagtcaacggattcaggaggccgcactctctg
5. Reverse Primer—SEQ ID NO: 5 5' atagcactaacagaagacagatcgctaa
6. BHQ1a labelled fam quenching primer—SEQ ID NO: 6 5' aggacgctagcacac-BHQ1a
7. BHQ1a labelled Joe quenching primer—SEQ ID NO: 7 5' agcgatgctaccgat-BHQ1a It will be noted that the Fam labelled quenching primer has 15mer oligonucleotide sequence and is more than 10 nucleotides shorter than the Fam labelled primer/reporter probe and similarly the Joe labelled quenching primer has a 15mer oligonucleotide sequence and is more than 10 nucleotides shorter than the Joe labelled primer/reporter probe. Accordingly, the longer Fam or Joe labelled primers/reporter probes have a Tm that is at or above the 57° C. Ta of the annealing step of the PCR process and will anneal with the amplicon in the process, whereas the shorter quenching primers are of Tm about 50° C., i.e. several degrees C. below the 57° C. Ta of the annealing step and will not anneal with the amplicon. All seven were synthesised by standard phosporamidite chemistry by Qiagen-Operon (Germany). All Oligos were diluted to 200 uM initial concentration in 10 mM Tris/HCl pH 8.0. All further dilutions were carried out in this diluent. An assay mix was created containing the following components:

| | |
|---|---|
| 0.25 uM | Allele Specific Primer 1 |
| 0.25 uM | Allele Specific Primer 2 |
| 1 uM | Reverse Primer |
| 0.1 uM | Fam labelled Primer |
| 0.1 uM | Joe labelled Primer |
| 0.5 uM | BHQ1a labelled Fam Quench Primer |
| 0.5 uM | BHQ1a labelled Joe Quench Primer |
| 0.2 Units | Titanium Taq (Becton Dickinson, UK) |
| 10 mM | Tris/HCL pH 8.3 |
| 50 mM | KCl |
| 0.05% v/v | IPEGAL -CA630 (Sigma Aldrich, Dorset UK) |
| 0.05% v/v | Triton X-100 (Sigma Aldrich, Dorset UK) |
| 2.2 mM | Magnesium Chloride |
| 200 uM | dNTP's (Sigma Aldrich, Dorset UK) |
| 5 uM | Rhodamine-X (Molecular Probes, Netherlands) |

To wells A1-B24 of a 384 well microtitre plate 10 ng of genomic DNA was added from 44 Caucasian individuals. The remaining 4 wells were left empty serving as negative control wells. This plate was then dried at 50 C for a period of 1 hour.

To wells A1-B24 of the dried plate 5 ul of assay mix was added and the plate sealed using an ALPS 300 plate sealer using clear seal strong (Abgene, Epsom UK). The plate was then thermal cycled under the following conditions in a mini-Duncan thermal cycler (Kbiosystems, Basildon, Essex UK).

94° C. for 4 mins followed by 20 cycles of the 94° C. denaturation temperature for 5 secs, 57° C. annealing temperature (Ta) for 10 secs, 72° C. elongation temperature for 20 secs, followed by a further 20 cycles of 94° C. for 5 secs, 57° C. for 20 secs, 72° C. for 40 secs Post thermal cycling the fluorescence associated with each well was determined using a Perkin Elmer, Envision plate reader (Turku, Finland). Each well was read three times at the following wavelength combinations.

| | | | |
|---|---|---|---|
| Fam excitation: | 485 nm | Fam emission: | 520 nm |
| Joe excitation: | 520 nm | Joe emission: | 560 nm |
| Rox excitation: | 590 nm | Rox emission: | 620 nm |

The resulting data was then plotted as Fam signal divided by Rox on the X axis, and Joe signal divided by Rox on the Y axis. This data is presented in FIG. 5. As can be seen from the scatter plot of FIG. 5 below, three clearly discernible groups associated with the respective genotypes are visible clearly demonstrating the effectiveness of the detection technology.

Figure 5:
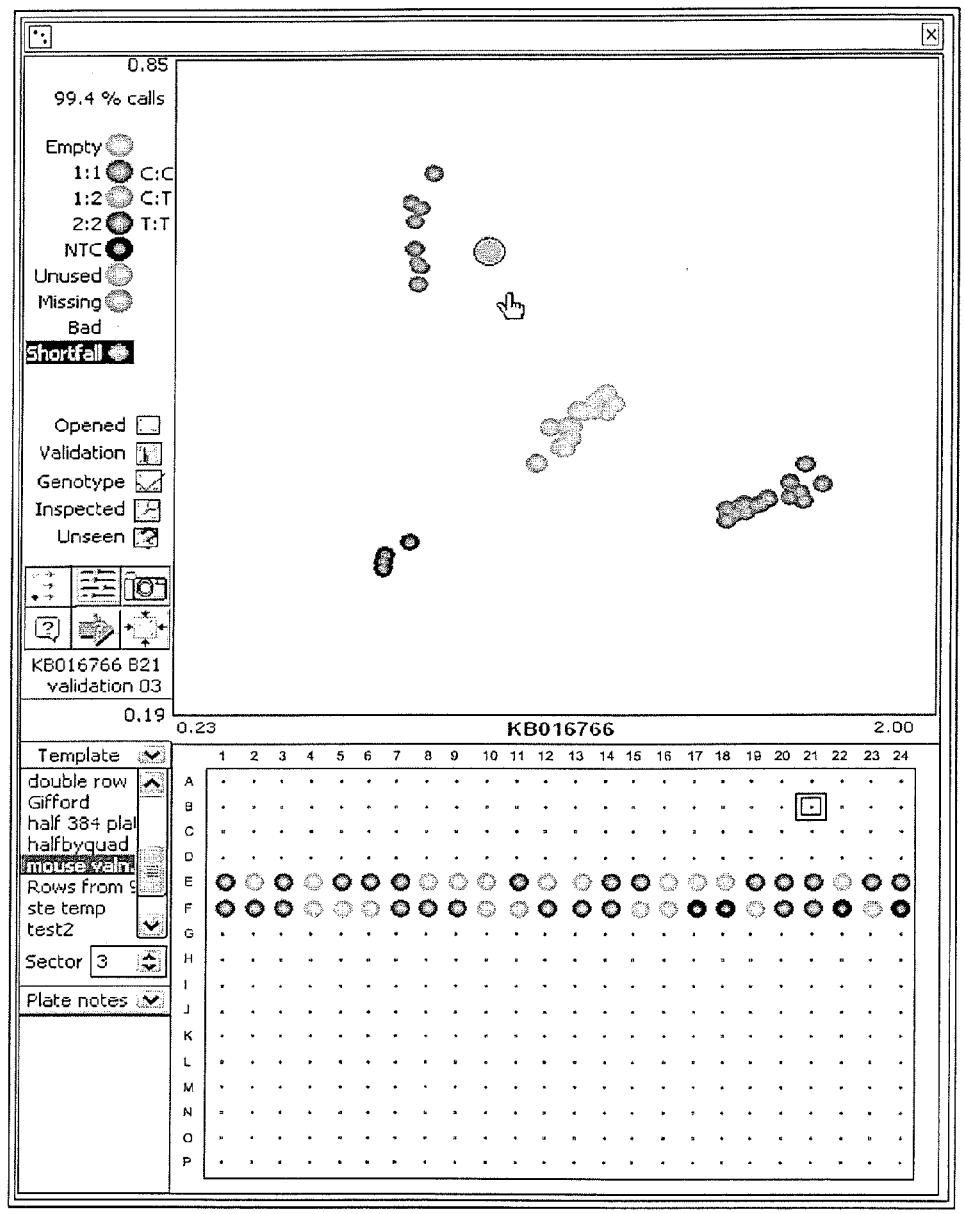
FIGS. 5 and 6 are, respectively, a graph of Fam signal divided by Rox on the X axis, and Joe signal divided by Rox on the Y axis and a graph of the analogous calculations from a nearly identical experiment showing the relative ineffectiveness of not using of a low Tm primer in the probe pair.
Figure 6:
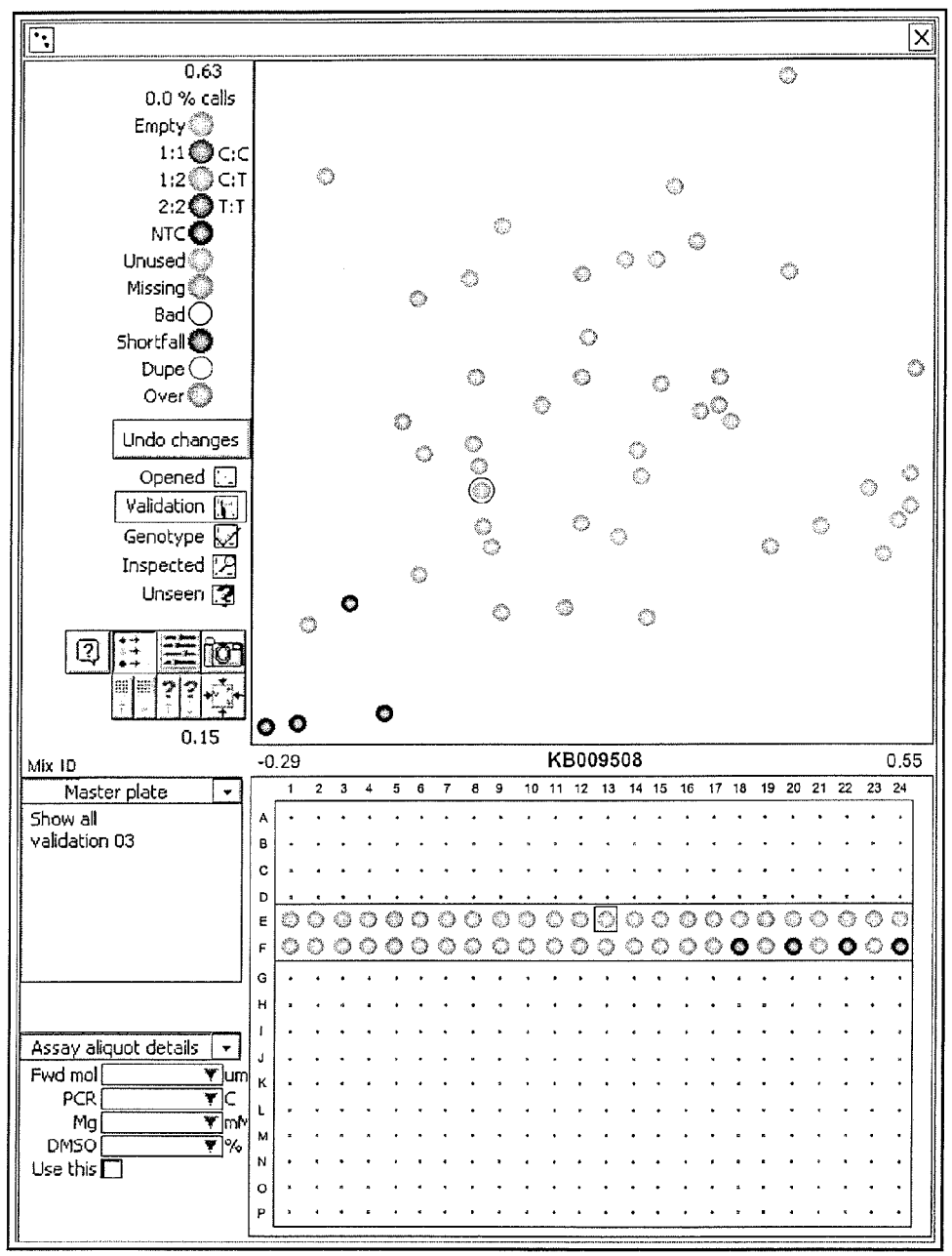

Turning to FIG. 6, an example of Allele Specific PCR based Genotyping is presented utilising two quenching oligos (one for each allele) in an identical experiment to that presented in FIG. 5. The only modification here is that the two quenching oligos were replaced with the longer, 18mer, base sequences below:

BHQ1a labelled Fam quenching primer 18mer—SEQ ID NO: 8 5' ttcaggacgctagcacac—BHQ1a BHQ1a labelled Joe quenching primer 18mer—SEQ ID NO: 9: 5' ttcagcgatgctaccgat—BHQ1a The data in FIG. 6 shows clear inhibition of the PCR process by the 18mer quenching oligos. The Tm of those 18mer quenching oligos is not below the 57° C. Ta of the PCR reaction. The contrast between these poor results and the very good results from the method as applied in FIG. 5 clearly demonstrates the dramatic benefit of utilising a low Tm form (sub Ta) of the second (e.g. quenching) primer of the pair of reporter primers/probes.

The second (e.g. quenching) oligonucleotide is effectively inert in the PCR process and thus no detrimental or inhibitory effects are seen. The increase in fluorescence is suitably ascertained by reading the reaction at a temperature below the Tm of the second oligonucleotide thus revealing the signal.

The invention claimed is:

1. A homogeneous assay detection system for a PCR process using FRET which comprises at least one unlabelled tailed primer, a first single-labelled Oligonucleotide sequence, the first single-labelled Oligonucleotide sequence being a primer from which DNA synthesis may be initiated, the unlabelled tailed primer having a tail region comprising an Oligonucleotide sequence identical to a portion of the first single-labelled Oligonucleotide sequence, and at least a second single-labelled Oligonucleotide sequence, the first and second Oligonucleotide sequences being of differing Tm, in which the first and second Oligonucleotide sequences hybridize to one another in free solution to form a fluorescent quenched pair, that upon introduction of a complementary sequence to one or both sequences at least one of the single-labelled Oligonucleotides hybridizes to a complementary sequence and initiates DNA synthesis, the said at least one single-labelled Oligonucleotide no longer being able to hybridize to the other single-labelled Oligonucleotide, whereby one or both sequences generates a measurable signal, one of the sequences being of a Tm that is below the Ta of the PCR process.

2. A detection system as claimed in claim 1, incorporated in a PCR system to detect a specific sequence, wherein said first single-labelled Oligonucleotide sequence and second single-labelled Oligonucleotide sequence differ by more than 10 bases in length.

3. A detection system as claimed in claim 1, wherein the introduction of a complementary sequence is by the production of DNA sequences via PCR.

4. A detection system as claimed in claim 1, wherein the PCR process is monitored in real time at each cycle or after a number of cycles whereat the reaction has otherwise not yet generated enough product to create a measurable signal by lowering the temperature of the reaction to allow hybridization to occur.

5. A detection system as claimed in claim 1, wherein said first sequence has a Tm that is above the Ta of the PCR process.

6. A detection system as claimed in claim 1, wherein said second sequence has the quencher label of the fluorescent quenched pair.

7. A detection system as claimed in claim 1, wherein the PCR process is allele specific PCR based SNP Genotyping.

8. A detection system as claimed in claim 2, wherein the PCR process is monitored via the use hybridization only.

9. A detection system as claimed in claim 8, wherein the PCR process is monitored via the use hybridization only post PCR.

10. A detection system as claimed in claim 1, wherein the fluorescent quench oligo pairs range from 6 bp to 100 bp.

11. A detection system as claimed in claim 10, wherein the fluorescent quench oligo pairs range from 6 bp to 100 bp but are not matched in length.

12. A detection system as claimed in claim 1, wherein the fluorescent quench oligo pairs are labelled both with fluorophores.

13. A detection system as claimed in claim 1, wherein the fluorescent quench oligo pairs are labelled one of the pair with a fluorophore and the other with a non fluorescent quenching molecule.

14. A detection system as claimed in claim 1, wherein the fluorescent quench oligo pairs are modified to be resistant to nuclease degradation.

15. A detection system as claimed in any preceding claim, wherein the fluorescent quench oligo pairs are labelled with molecules that are distant sensitive.

16. A detection system as claimed in claim 15, wherein the PCR process is monitored via the use of hybridization only.

17. A detection system as claimed in claim 1, wherein the fluorescent quench oligo pairs contain modified nucleotide bases.

18. The detection system as claimed in claim 1, in which the first single-labelled Oligonucleotide primer sequence has an unmodified 3' base from which DNA synthesis is initiated.

19. A detection system as claimed in claim 1, further comprising at least one unlabelled tailed primer, the tail comprising a DNA sequence identical to a portion of the first single-labelled Oligo sequence.

* * * * *

UNITED STATES PATENT AND TRADEMARK OFFICE
CERTIFICATE OF CORRECTION

PATENT NO. : 7,615,620 B2 Page 1 of 1
APPLICATION NO. : 11/443547
DATED : November 10, 2009
INVENTOR(S) : Philip S. Robinson It is certified that error appears in the above-identified patent and that said Letters Patent is hereby corrected as shown below:

The errant designation "REPLACEMENT SHEET" is deleted from drawing sheet number two, Fig. 1B, part 4.

Signed and Sealed this

Twenty-third Day of February, 2010

David J. Kappos
*Director of the United States Patent and Trademark Office*